United States Patent [19]

Gehlke et al.

[11] Patent Number: 4,542,434
[45] Date of Patent: Sep. 17, 1985

[54] METHOD AND APPARATUS FOR SEQUENCED BIPOLAR AIR IONIZATION

[75] Inventors: Scott J. S. Gehlke; Michael G. Yost; Arnold J. Steinman, all of Berkeley, Calif.

[73] Assignee: Ion Systems, Inc., Berkeley, Calif.

[21] Appl. No.: 581,421

[22] Filed: Feb. 17, 1984

[51] Int. Cl.$^4$ .............................................. H05F 3/06
[52] U.S. Cl. ................................... 361/231; 361/213; 361/235
[58] Field of Search ............... 361/212, 213, 215, 229, 361/230, 231, 232, 235

[56] References Cited

U.S. PATENT DOCUMENTS

| | | | |
|---|---|---|---|
| 2,264,495 | 6/1937 | Wilner | 175/265 |
| 3,624,448 | 11/1971 | Saurenman | 361/235 X |
| 3,711,743 | 1/1973 | Bolasny . | |
| 3,936,698 | 2/1976 | Meyer . | |
| 4,351,648 | 9/1979 | Penney | 55/137 |

OTHER PUBLICATIONS

3M Corporation brochure entitled "911 Heated Ionized Air Blower" and carrying no date (2 pages).
Don Yenni, "Basic Electrical Considerations in the Design of a Static–Safe Work Environment, dated 1979, (12 pages).
James R. Huntsman et al., "Charge Drainage vs Voltage Suppression by Static Control Table Tops", Mar. 1982 (3 pages).
L. J. Herauf, "Measurement of Ion Distribution in Ionized Air" (carries no date) (2 pages).
Sales brochure of Ion Systems, Inc., entitled "IONOSPHERE The Ultimate Air Purifier" and carrying no date (1 page).

Primary Examiner—Harry E. Moose, Jr.
Attorney, Agent, or Firm—Phillips, Moore, Lempio & Finley

[57] ABSTRACT

Positive and negative ion contents of the air within a region are controlled to suppress build-up of electrostatic charges on objects or for other purposes with one or more air ionizing units each having a positive high voltage generator coupled to a first ionizing electrode and a negative high voltage generator coupled to a second spaced apart ionizing electrode. The positive and negative high voltage generators are operated alternately with off times being provided between each period of ion generation of either polarity and the preceding period of generation of ions of the opposite polarity. The off times enable ions of each polarity to disperse outwardly for a controlled distance before substantial intermixing and mutual neutralization takes place. In the preferred form of the invention, the durations of the positive and negative ion generation periods, the off times between such periods and the rates at which each type of ion generation occurs during such periods are each separately controlled to accommodate to different ion requirements of different rooms or to changed conditions in a particular room.

16 Claims, 4 Drawing Figures

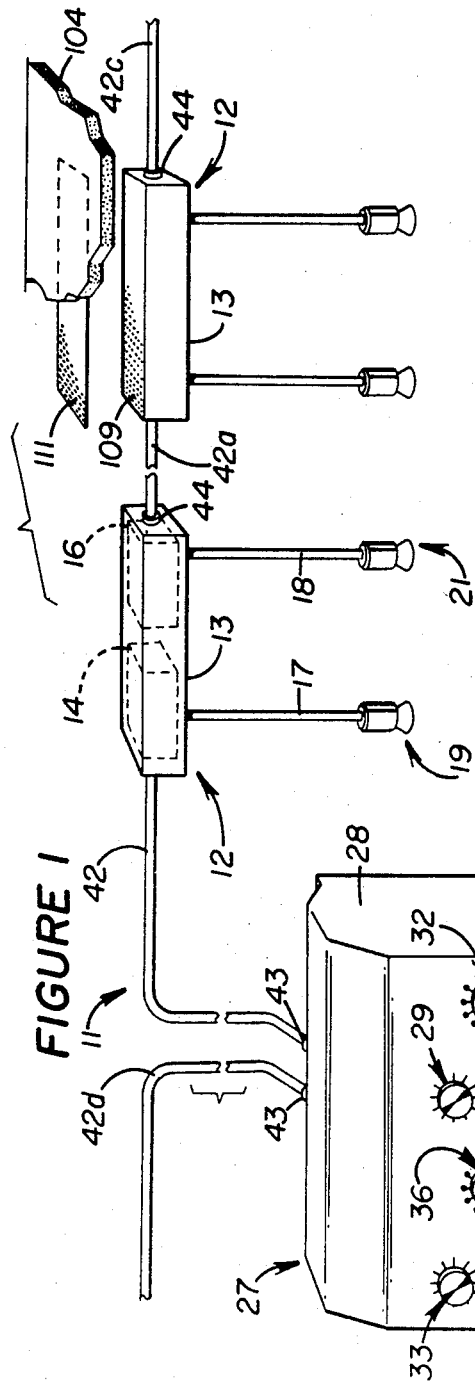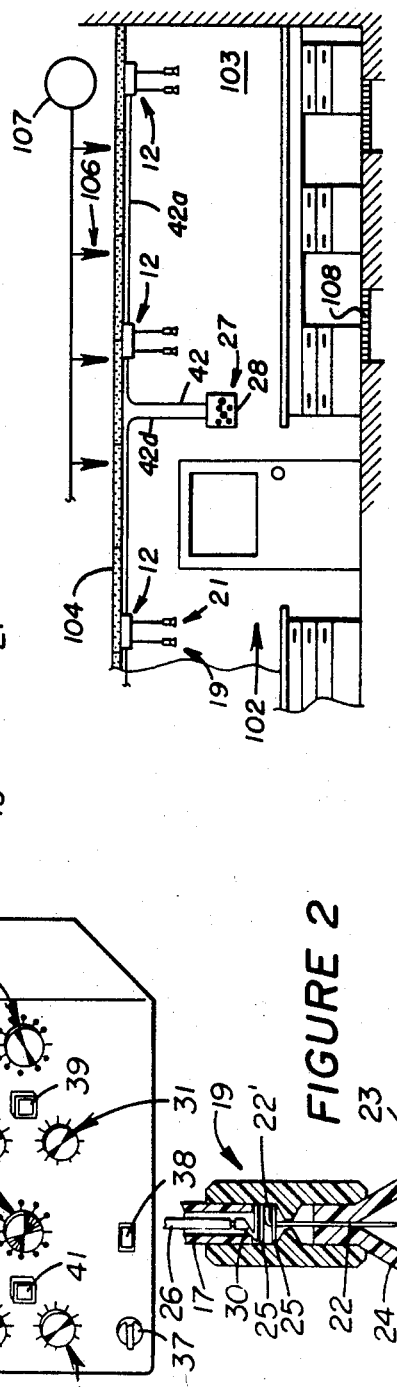

METHOD AND APPARATUS FOR SEQUENCED BIPOLAR AIR IONIZATION

TECHNICAL FIELD

This invention relates to methods and apparatus for generating ionized air and more particularly to a method and apparatus for controlling the concentration of both positive and negative air ions within a predetermined region.

BACKGROUND OF THE INVENTION

Individual molecules of the gases which constitute air can acquire an electrical charge and become positive or negative ions depending on whether a deficiency or an excess of electrons has been imparted to the molecule. Some ions of each type are usually present in outdoor air as a result of static electricity discharges and other natural causes. The degree of air ionization and the relative proportions of positive and negative ions vary widely under natural conditions in response to changes in atmospheric and environmental factors.

A relatively high level of air ionization has beneficial effects. Ions tend to remove particulate contaminants, such as smoke particles or pollens for example, from air by transferring charge to such particles. The charged particles are then electrically attracted to nearby surfaces that are electrically neutral or oppositely charged and are deposited against such surfaces. Air rich in negative ions in particular is also believed to have beneficial physiological effects.

Air inside buildings tends to become stale and unpleasant to breathe, the effect being attributable at least in part to depletion of the ion content. A variety of air ionizers have heretofore been developed to counteract this effect and also to purify air by removing particulate contaminants in the manner previously described. Typically, such air ionizers have an electrode coupled to a D.C. high voltage source and having one or more sharp points. The intense electrical field adjacent the point or points breaks down nearby gas molecules to form positive or negative ions depending on the polarity of the high voltage. Electrostatic repulsion from the similarly charged electrode and from each other, together with electrostatic attraction to neutral objects such as the walls of the room, then causes such ions to disperse outwardly from the ionizer. Air blowers are sometimes provided to accelerate such dispersion and to extend the effective range of the ionizer.

Ionizers designed specifically for the above described purposes usually produce only the physiologically beneficial negative ions. Another, increasingly important application of air ionizers requires that ions of both polarities be generated. In particular, air ionizers can also be extremely useful for suppressing build-up of electrostatic charges on objects in a room.

Objects, including humans, situated in a room very often acquire a sizable electrostatic charge which may have a magnitude of several thousand volts or more. Such charging of non-conductive objects may be caused by movement and the accompanying friction while induction and discharges from other objects may impart charge to ungrounded conductors. Sizable electrostatic charge accumulations of this kind can be highly undesirable for a number of reasons. Sudden discharges, although not usually harmful, are distinctly unpleasant to people. Electrostatic charge can also interfere with the operation of electrical devices ranging from phonographs to computers.

Problems caused by electrostatic charge build-up have become particularly acute in the manufacture of certain products such as in facilities, known as clean rooms, in which miniaturized semiconductor circuit components are fabricated. Static discharges frequently damage or destroy the minute conductive paths in microcircuits or the like and the electric field associated with electrostatic charge can have other adverse effects as well. Dust particles or other contaminants, for example, are attracted to a charged area of a semiconductor wafer or the like and then adhere to the area by electrostatic attraction. Suppression of electrostatic charge build-up is a practical necessity in clean rooms to avoid unacceptably high product losses. For this purpose, a variety of techniques are utilized in combination. Careful arrangements are made for the grounding of conductive or somewhat conductive objects in the room including personnel and antistatic structural materials and specialized clothing are usually utilized. Establishing and maintaining a high level of air ionization is also recognized to be a very effective technique for suppressing electrostatic charge.

An accumulation of electrostatic charge on an object can be neutralized by charge exchange with air ions of opposite polarity which are attracted by the electrical field associated with the electrostatic charge. A high level of both positive and negative ions is most effective for this purpose as the electrostatic charges to be neutralized may be of either polarity. Prior bipolar air ionizers and the methods under which such ionizers are operated are not as effective for this purpose, or for certain other purposes, as would be desirable.

Some prior procedures and apparatus that produce air ions of both polarities are intended to impart electrostatic charges to objects. Prior U.S. Pat. No. 3,936,698, for example, teaches the treatment of medical patients by cyclically directing negative ions from a first ionizing electrode to the patient for intervals of the order of five minutes during which the patient acquires a negative charge. Positive ions from a second electrode are then directed at the patient between such periods to remove the electrical charge. Such procedures are obviously at cross purposes with the objective of suppressing charge build-up on objects.

Other prior systems for generating air ions at both polarities that are intended for electrostatic charge suppression and/or for air freshening or purification employ much higher cycling rates or indeterminate cycling rates. Prior U.S. Pat. No. 3,711,743, for example, discloses a method and apparatus for controlling electrostatic charge in which a single ionizing electrode is switched between positive and negative high voltage states at a frequency ranging from 60 cycles per second up to 10 KHz. U.S. Pat. No. 2,264,495 teaches switching of a single ionizing electrode between positive and negative ion generation in response to sensors which detect variations in the concentrations of both types of ions in incoming air in order to maintain a predetermined ratio.

Systems of the latter type are effective for controlling air ion concentrations within an adjacent region but the distance or range at which such control is realized is undesirably limited. Ions of opposite polarity are electrostatically attracted and can then neutralize each other by charge exchange. In devices of the above discussed type, outward dispersion of the ions tends to be relatively slow in relation to the cycling time. Intermixing of the alternating groups of positive and negative ions and consequent neutralization begins in the immediate vicinity of the ionizing electrode and progresses rapidly as the ions disperse outwardly. Thus the ion content in the air falls off rapidly at increasing distances from the ionizer. The effect is most pronounced where both types of ion are generated at the same electrode but also occurs to an undesirable extent in prior systems having separate, spaced apart pairs of electrodes each of which generates a single type of ion.

Various techniques have heretofore been used to extend the effective range of such ionizers but such measures are of limited effectiveness or are subject to other problems. It is a common practice, for example, to provide an air flow past the ionizing electrode with a blower or by situating the electrode in a pre-existing air flow in order to accelerate the movement of newly generated ions away from the ionizer. While this is effective up to a point, the rate of air flow must usually be limited to avoid discomfort of personnel and dislocation of light unattached objects in the room. In another approach to the problem, a large number of ionizing electrodes are arrayed on a supporting gridwork which spans the region in which static charges are to be suppressed, each electrode being connected to the alternating high voltage supply through high voltage cables. If it is sufficiently large, such a system can blanket an area with air ions but it is also bulky, costly and cumbersome to install. The ion neutralization problem remains except insofar as it is compensated for by increased ion production at an increased number of different locations.

Prior systems for generating both positive and negative air ions also tend to be inflexible with respect to accommodating to the needs of different rooms, different specific locations in a particular room and changing conditions in a particular room. Electrostatic charges to be neutralized are not necessarily evenly balanced as between positive charges and negative charges. One type or the other may predominate in a particular room and there may be differences in this respect between different specific locations in the room. Further, the amounts and polarities of static charges to be neutralized within a particular room may change as work operations and the types and locations of equipment are changed. Ionizing systems which generate fixed levels of positive and negative ions in equal amounts or at a fixed ratio during successive fixed time periods cannot function in the most effective manner where variations of these kinds are encountered.

The present invention is directed to overcoming one or more of the problems set forth above.

SUMMARY OF THE INVENTION

In one aspect, the present invention provides a method of controlling the ion content of air within a predetermined region which includes the steps of periodically generating positive air ions at a first location and periodically generating negative air ions at a second spaced apart location during the intervals between periods of positive ion generation and in which the positive and negative ions disperse outwardly from the first and second locations respectively and intermix within the predetermined region. The intermixing of the ions is delayed by delaying each period of ion generation for a predetermined time interval following termination of the preceding period of ion generation.

In another aspect of the method, the distance from the first and second locations at which the ions become intermixed is controlled by selection of the durations of the predetermined time intervals between periods of ion generation.

In still another aspect, the method of the present invention provides for adjusting the concentrations of positive and negative ions in the air at a predetermined region and includes the steps of generating positive ions at a first location during repetitive time periods of selected duration, generating negative ions at a second spaced apart location during repetitive time periods of selected duration that alternate with the periods of positive ion generation, delaying each period of ion generation at the first location for a selected time interval following the preceding period of ion generation at the second location, and delaying each period of ion generation at the second location for a selected time interval following the preceding period of ion generation at the first location.

In another aspect, the invention provides apparatus for controlling the concentrations of positive and negative ions within a volume of air, having at least one pair of spaced apart air ionizing electrodes including a positive electrode and a negative electrode, means for applying positive high voltage to the positive electrode, means for applying negative high voltage to the negative electrode, and control means for cyclically and alternately actuating the positive high voltage means and the negative high voltage means. The apparatus further includes means for delaying each actuation of the positive high voltage means for an interval following the preceding actuation of the negative high voltage means, and means for delaying each actuation of then negative high voltage means for an interval following the preceding actuation of the positive high voltage means.

In another more specific aspect, the invention provides apparatus for controlling air ion content within a region and includes at least a pair of spaced apart air ionizing electrodes each having at least one sharp point exposed to the air, a positive high voltage generator connected to a first of the electrodes, a negative high voltage generator connected to the second of the electrodes, first control means for selecting a first ion generation delay period, second control means for selecting a second ion generation delay period, third control means for selecting a positive ion generation period, fourth control means for selecting a negative ion generation period, and timing circuit means for alternately actuating the positive high voltage generator and the negative high voltage generator to produce a repetitive ion generation cycle during which positive ions are generated for the positive ion generation period and then ion generation ceases for the first delay interval after which negative ions are generated for said negative ion generation period and then ion generation ceases for said second delay interval.

By providing off intervals between alternating periods of positive and negative ion generation at spaced apart electrodes, the invention enables desirably high ion concentrations of both polarities to be established and maintained at extended distances from the ionizer which distances are controllable in the preferred embodiment of the invention. Preferred embodiments of the invention also provide for separate adjustment of the durations of the positive and negative ion generation periods, the delay intervals between such periods and the rates at which each type of ion are generated during such periods. This enables more precise control of ion concentrations and the relative proportions of each type of ion needed for electrostatic charge suppression and/or other purposes in different rooms or under changing conditions in a specific room. The preferred form of the invention further enables sequenced bipolar ion generation at a large number of separate locations within a room with apparatus which is compact, economical, easily installed and which does not necessarily require extensive lengths of high voltage cable.

BRIEF DESCRIPTION OF THE DRAWINGS

FIG. 1 is a perspective view of a sequenced bipolar ionizing system in accordance with a preferred embodiment of the invention.

FIG. 2 is a section view of a portion of the apparatus of FIG. 1 illustrating a suitable construction for the air ionizing electrodes thereof.

FIG. 4 is an elevation view of a portion of a room in which electrostatic charges are to be suppressed and which illustrates a typical installation of the apparatus of the preceding figures.

DETAILED DESCRIPTION OF A PREFERRED EMBODIMENT

Figure 3:
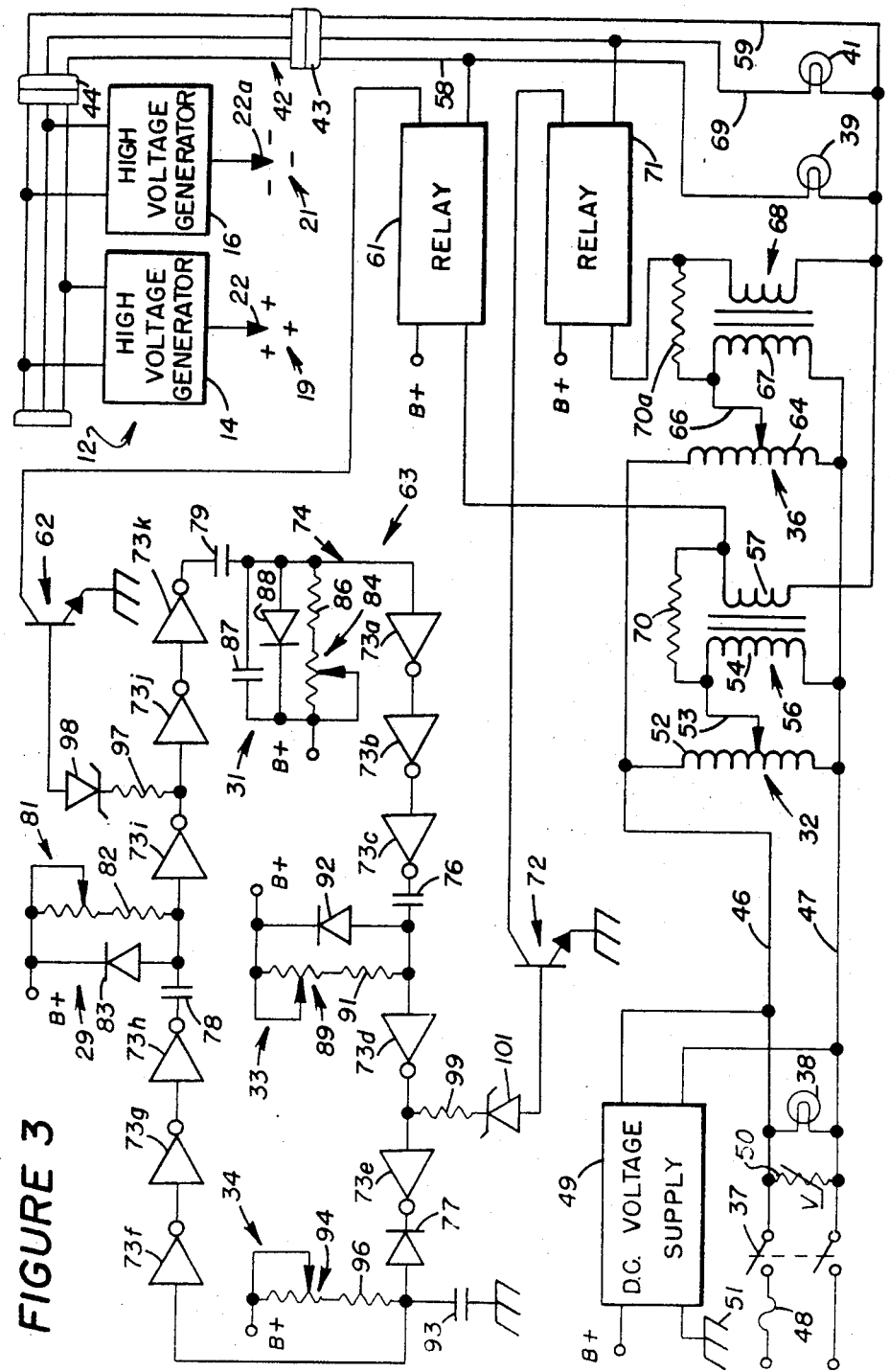
FIG. 3 is an electrical circuit diagram of the control and timing components of the apparatus of FIGS. 1 and 2.

Referring initially to FIG. 1 of the drawings, the ionizer apparatus 11 of this particular example of the invention includes a series of individual ionizing units 12 which are situated at spaced apart locations in a room as will hereinafter be described in more detail. A single ionizing unit 12 may be used where air ion content is to be controlled only within a small region but more typically a larger number of such units are utilized.

Each ionizing unit 12 has a separate housing 13, of rectangular configuration in this example, which contains a positive high voltage generator 14 and a negative high voltage generator 16 of the known type that are energized or actuated by relatively low voltage alternating current and which produce high voltages having magnitudes proportional to the magnitude of the voltages of the alternating current. In the present example, high voltage generators 14 and 16 are of a type that produces voltages in the range from 3 KV to 20 KV in response to actuating current voltages in the range from 8 to 48 volts although these values should not be taken to be limitative of the possible operating parameters of the system.

A pair of spaced apart parallel insulative rods 17 and 18 extend from each ionizing unit housing 13 to support positive and negative ion emitters 19 and 21 respectively in spaced apart relationship.

Referring now to FIG. 2, rod 17 extends into the upper end of an insulative sleeve 20 and a conical insulative electrode guard 24 extends from the lower end of the sleeve. The air ionizing electrode 22 in this example is a stainless steel surgical needle extending along the axis of guard 24 and having a sharp point 23 situated just below the lower end of the guard. Electrode 22 has an angled upper end 22' received between two conductive washers 25 within sleeve 20 which are pressed together by the lower end of rod 17 through an angled contact lug 30. Lug 30 connects to a high voltage conductor wire 26 which extends upward within rod 17 to the high voltage generator 14 of FIG. 1. Other emitter and electrode constructions may also be employed.

The construction of the negative emitter 21 is similar to that of positive emitter 19 except insofar as it is connected to negative high voltage generator 16.

The components 19 and 21 have been herein termed "emitter" in keeping with established terminology in the art but it should be recognized that electrodes 22 do not emit air ions in the strict sense of the word. Rather, when charged to a high voltage, the electrodes 22 exhibit an electrical field which is most intense in the region immediately adjacent the sharp point 23. The intense field disrupts the normal charge state of molecules of air gases, such as nitrogen and oxygen, at that region and the molecules then become negative or positive ions depending on whether the molecule has acquired an excess or a deficiency of electrons. Ions of opposite polarity from the high voltage on electrode 22 are attracted to the electrode and neutralized. Ions of the same polarity as the high voltage are electrostatically repelled by the electrode and disperse outwardly, the dispersal process being aided by elctrostatic attraction to neutral or oppositely charged objects in the vicinity such as the walls of a room for example. Thus a cloud of air ions, of the same polarity as the voltage on electrode 22, flow outwardly from the electrode during periods in which high voltage is present on the electrode.

Referring again to FIG. 1, the generation of both positive and negative ions poses problems with respect to providing desirably high levels of ion content in the air at desirable distances from the ionizing units 12. Ions of opposite polarities are attracted together and may then neutralize each other by charge exchange. The separation of the positive and negative emitters 19 and 21, which is approximately 20.5 centimeters in this particular example although other spacings may also be employed, aids in delaying intermixing of the oppositely charged ions but extreme spacings are often not feasible or desirable as each of the emitters 19 and 21 is surrounded by a zone in which electrostatic charge is actually imparted to objects and the extent of this zone is in part a function of the emitter spacing. The extent of such zones needs to be restricted to small areas in which imparted charges will not pose problems. Thus additional procedures are needed to enable outward dispersal of each type of ion for extended distances before substantial intermixing and mutual neutralization occurs. Preferably such procedures should enable adjustment of the distance at which such intermixing occurs.

In accordance with the method of the present invention, the positive emitters 19 and negative emitters 21 of each ionizing unit 12 are actuated during repetitive alternating time periods by alternately actuating the positive high voltage generators 14 and the negative high voltage generators 16. Thus positive ions disperse away from emitters 19 during periods which alternate with periods during which negative ions disperse away from emitters 21. Intermixing of the two types of ions is delayed, to locate the region of intermixing a desirable distance outward from the emitters 19 and 21, by delaying each of the periods of ion generation for a predetermined timed interval following the preceding period of ion generation. Thus each period of either positive or negative ion generation is followed by an off interval during which no ions of either type are generated. Thus each cloud of generated ions may travel outwardly for a controlled distance before expansion of the cloud and slowing and randomization of ion drift results in intermixing with previously generated ions of opposite polarity.

In the preferred practice of the invention, the duration of the periods of positive ion generation, the duration of the off intervals which follow positive ion generation, the duration of the negative ion generation periods, the duration of the off intervals which follow negative ion generation, the rate at which positive ions are generated during the positive ion generation periods and the rate at which negative ions are generated during the negative ion generation periods are each separately selected and controlled and need not necessarily be the same. This enables different ratios and concentrations of the two types of ion to be established at controlled distances according to the specific requirements of each particular usage of the system or to adjust to changing conditions at a particular location. For example, some clean rooms may exhibit more negative static charges than charges of the opposite polarity and thus suppression of static charge build-up in the particular rooms requires a relatively high level of positive air ions. The amounts of static charge accumulation may vary from room to room or at different times in the same room and thus the rate of generation of ions needs to be varied accordingly.

The durations of the periods of ion generation are selected from a range of about 0.5 seconds to about 10 seconds according to the needs of the particular room. Shorter on times or ion generation periods do not allow for an effective amount of ion generation. On times or ion generation periods longer than about 10 seconds create an impractically large zone around the ionizing units 12 in which static charge may actually be imparted to objects.

The delay intervals or off times between successive periods of ion generation are also selected to be in the range from about 0.5 second to about 10 seconds. Delay periods shorter than about 0.5 second allow intermixing of the two types of ion in the immediate vicinity of the emitters 19 and 21 thereby restricting the effective range of the ionizing units 12 to undesirably short distances. Delay intervals exceeding about 10 seconds may allow an unacceptable build-up of static charges on objects in the room.

The above stated range of on times and off times durations takes into account the effects of air flow rate past the emitters 19 and 21. As will hereinafter be discussed in more detail, an air flow is usually provided to accelerate the outward dispersal of ions from the emitters 19 and 21. Shorter ion generation periods and delay intervals or off times are used in the presence of more rapid air flow if the region of intermixing of positive and negative ions is to be maintained at a constant distance from the emitters 19 and 21. The ion generation periods and delay intervals are not, as a practical matter, reduced below about 0.5 second by increasing air flow rate as the necessarily high rates of flow become discomforting to personnel and may dislocate papers and other light objects in the room.

Referring still to FIG. 1, control means 27 for repetitively cycling the apparatus 11 to accomplish the above described operations are contained in a control circuit housing 28 which need not necessarily be located in the immediate vicinity of the ionizing units 12. Manually adjustable controls on the face of housing 28 in this embodiment include positive on time selector means 29 for selectively changing the duration of the periods of positive ion generation, positive off time shorter means 31 for selectively changing the duration of the delay or off intervals which follow each period of positive ion generation and positive high voltage selector means 32 for selectively changing the rate or output of positive ion generation. Similar controls for the negative portion of the operating cycle include negative on time selector means 33 for selectively changing the duration of the periods of negative ion generation, negative off time selector means 34 for selectively changing the duration of the delay or off intervals which follow each period of negative ion generation and negative high voltage selector means 36 for selectively changing the rate or output of negative ion generation. A power on-off switch 37 and and power on indicator lamp 38 are also mounted on the face of the housing 28. To enable visual monitoring of the cycling of the apparatus 11, additional lamps 39 and 41 are provided on the housing 28 to indicate periods of positive ion generation and periods of negative ion generation respectively. The electrical circuit within housing 28 and the interaction of the several external control means 29, 31, 32, 33, 34 and 36 therewith will be hereinafter described.

Electrical power for actuating and operating the high voltage generators 14, 16, is transmitted to a first of the ionizing units 12 through a first length 42 of three wire insulated cord conductor which connects to control means 27 at a first plug connector 43 on housing 28. Additional lengths 42a, 42c of such cord conductor transmit operating power onto each successive one of the ionizing units 12 through additional plug connectors 44 at each end of each such unit. To facilitate the connection of a large number of ionizing units 12, at varying locations in a room, to the control means 27, housing 28 of this embodiment is provided with a second plug connector 43 into which another length 42d of the cord conductor may be connected to transmit operating power to ionizing units 12 that may be located in an opposite direction from those depicted in FIG. 1. The several lengths of cord conductor 42 need not be high voltage cables, which are costly and difficult to install, as the high voltage generators 14, 16 are located at the individual ionizing units 12 and are operated with relatively low voltage input currents.

Referring now to FIG. 3, the control circuit of this embodiment operates from standard utility 115 volt alternating current received on conductors 46 and 47 through the power on-off switch 37 and a protective fuse 48. Power on indicator lamp 38 is connected across conductors 46 and 47. A varistor 50, also connected across conductors 46 and 47, protects the circuit against power surges and transients that may occur on power lines. To provide operating power for solid state circuit components to be hereinafter described, a D.C. voltage supply 49 is also conected between conductors 46 and 47 and may be of the known form which reduces, rectifies and smooths the A.C. voltage to produce a direct output of 15 volts in this particular example. The D.C. voltage is produced at an output terminal B+, the other output terminal of D.C. voltage supply 49 being connected to chassis ground 51. Symbol B+ in FIG. 3 indicates a connection to the similarly indentified terminal of D.C. voltage supply 49.

The previously described positive high voltage selector means 32 includes a first Variac or autotransformer 52 connected across conductors 46 and 47 and having a manually adjustable output tap 53 connected to conductor 47 through the primary coil 54 of a first step down transformer 56 which, in the present embodiment, produces A.C. voltages ranging from zero to 48 volts depending on the setting of Variac 52. The secondary or output coil 57 of transformer 56 is connected across first and second low voltage lines 58 and 59 respectively in series with a first normally open relay 61 which is preferably of the solid state type.

The first relay 61 is operated by B+ voltage and closes in response to conduction of relay driver current through a first NPN transistor 62 which has a grounded emitter and a collector connected to the relay. The transistor 62 is cyclically turned on and off, to repetitively close and open relay 61, by a timing circuit 63 which will hereinafter be described.

The periodic closings of relay 61 cause the low voltage output of transformer 56 to be periodically applied to the first and second low voltage lines 58 and 59 which extend, through the previously described cord conductor 42, to each of the ionizing units 12 in the system. The positive high voltage generator 14 of each such ionizing unit 12 is connected across the first and second low voltage lines 58 and 59 and thus each such unit is actuated to produce positive air ions during the periodic closings of relay 61. The magnitude of the positive high voltage produced by generators 14 and thus the positive ion generation rate and output during such periods is dependent on the voltage of the A.C. current on lines 58 and 59 and is therefore selectable by adjustment of tap 53 of Variac 32.

Circuit components for periodically actuating the negative high voltage generators 16 of the ionizing units 12 are essentially similar to those described above with respect to positive ion generation. Thus the negative high voltage selector means 36 includes a second Variac or autotransformer 64 connected across conductors 46 and 47 and having an adjustable output tap 66 connected to conductor 47 through the primary coil 67 of a second step down transformer 68. The output or secondary coil of transformer 68 is connected between the second low voltage line 59 and a third low voltage line 69 in series with a second relay 71. The second relay 71 is operated by B+ voltage and closes to apply alternating current to conductor 69 in response to conduction through a second NPN transistor 72 which is periodically turned on or conductive by timing circuit 63 as will hereinafter be described in more detail.

The third low voltage line 69 also extends through cord conductor 42 to each of the ionizing units 12 in the system and the negative high voltage generator 16 of each such unit is connected across the second and third low voltage lines 59 and 69 respectively. Thus the periodic closings of second relay 71 cause negative ion generation at each ionizing unit 12 in a manner essentially similar to that previously described with reference to positive ion generation, the negative ion generation rate and output being selectable by adjustment of Variac tap 66 in this case.

As there is otherwise no conductive path connecting the high voltage generators 14 and 16 to a voltage reference point, high voltage return paths are established by high resistances 70 and 70a of one megohm rating in this example which are connected across the primary and secondary sides of transformers 56 and 68 respectively.

The timing circuit 63 in this embodiment of the invention includes eleven inverters 73a to 73k connected in series to define a closed loop signal path 74. Each of the inverters 73a to 73k is an inverting amplifier of the known form in which the output voltage switches between a low condition and a relatively high condition, the output voltage being low when the input voltage is high and being high when the input voltage is low. In the present example, the inverters 73a to 73k are MC14049UB Hex Inverters manufactured by Motorola Inc., Phoenix, Ariz. although other similar components may also be used.

For reasons which will become apparent when the operation of timing circuit 63 is described, the connection between inverters 73c and 73d in particular is through a capacitor 76. The connection between inverters 76e and 76f is through a diode 77 oriented to block direct transmission of positive signal voltage from inverter 76e to inverter 73f. Inverter 73h is coupled to inverter 73i through a capacitor 78 and inverter 73k is coupled to inverter 73a through another capacitor 79.

The previously described transistor 62 which initiates the periods of positive ion generation is controlled by the output of inverter 73i in particular. For this purpose, the base of the transistor 62 receives the output signal voltage of inverter 73i through a resistor 97 and zener diode 98. Zener diode 98 is oriented to block the low signal output of inverter 73i from transistor 62 and to transmit the high signal output of the inverter to the transistor to cause conduction therethrough. Thus transistor 62 is on when the output of inverter 73i is high and off when the inverter output is low.

Transistor 72 which initiates the periods of negative ion generation is controlled in a similar manner by the output signal from inverter 73d through another resistor 99 and zener diode 101. Thus transistor 72 is on when the output of inverter 73d is high and off when the inverter output is low.

The positive on time selector means 29 for changing the duration of the periods of positive ion generation includes a manually adjustable variable resistance 81 and fixed resistance 82 connected in series between the B+ terminal and the input side of inverter 73i. A diode 83 is connected in parallel with resistances 81 and 82 to suppress voltage transients.

Positive off time selector means 31 for changing the delay interval which follows positive ion generation also includes a manually adjustable variable resistor 84 and a fixed resistance 86 which are connected in series between the B+ terminal and the input of inverter 73a and also includes a diode 88 connected in parallel with the resistances. An additional relatively small capacitor 87 is connected between the B+ terminal and the input of inverter 73a, in parallel with resistances 84 and 86 to set the timing circuit 63 at start up as will hereinafter be described.

Negative on time selector means 33 for changing the duration of the negative ion generation periods has a similar manually adjustable variable resistance 89 and fixed resistance 91 connected in series between the B+ terminal and the input of inverter 73d with another diode 92 being connected in parallel with the resistances. Negative off time selector means 34 for changing the delay interval which follows a period of negative ion generation has still another manually adjustable variable resistance 94 and fixed resistance 96 which are connected in series between the B+ terminal and the input to inverter 73f. The input to inverter 73f is also coupled to chassis ground 51 through a capacitor 93.

In operation, the timing circuit 63 is essentially a system in which changes of inverter output state repetitively circulate around the closed loop signal path 74 subject to controlled delays determined by the settings of the four variable resistances 81, 84, 89 and 94. This results in transistor 62 being turned on for a period determined by variable resistance 81 which is followed by an off interval determined by variable resistance 84. Transistor 72 then turns on for a period determined by variable resistance 89 which is followed by another off interval determined by variable resistance 94. The cycle then continues repetitively until the power on switch 37 is opened although adjustments may be made at any time to change the duration of any of the on periods and off periods.

More specifically, at the closure of the power on switch 37 capacitor 87 transmits a pulse which initiates a high condition at the input of inverter 73a. The output of inverter 73a is then low which in turn causes the output of inverter 73b to be high which causes the output of inverter 73c to be low. The input of inverter 73d is also low although capacitor 76 begins to build-up positive charge at a rate determined by the setting of variable resistance 89. As the input of inverter 73d remains low until capacitor 76 has been charged up to the threshold voltage required to trigger a change of state in the inverter, the output remains high for a period causing transistor 72 to be turned on which initiates a period of negative ion generation in the manner previously described.

At the start up time described above, the high condition at the output of inverter 73d is transmitted on to inverter 73e which therefore has a low output. The input to inverter 73f is also low as a period of time, determined by variable resistance 94, is required for capacitor 93 to charge to a voltage level sufficient to cause a high condition at the input to inverter 73f. Owing to diode 77, such charging period does not begin until a later stage of operation when the output of inverter 73e switches to a high condition. Consequently, at the start up time, the output of inverter 73f is high, the output of inverter 73g is low and the output of inverter 73h is in the high condition. As the input to inverter 73i is high, the output is low and the transistor 62 which controls positive ion generation is off. The output of the next inverter 73j is high and therefore the output of inverter 73k is low.

The above described initial conditions change when capacitor 76 has charged sufficiently to cause the output of inverter 73d to go low and shut off transistor 101 thereby ending the period of negative ion generation. The output of the next inverter 73e is simultaneously caused to go high but the change of state does not immediately progress on to the following inverter 73f as the positive output signal from inverter 73e is blocked by diode 77. Capacitor 93, which has remained in a low state of charge by being connected to the low output of inverter 73e through diode 77, begins charging when the output of inverter 73e goes high and, after an interval determined by the setting of variable resistance 94, acquires a sufficiently high voltage to cause the output of inverter 73f to go low. This in turn causes the output of inverter 73g to go high which causes the output of inverter 73h to go low and the output of inverter 73i then goes high turning on transistor 62 and initiating a period of positive ion generation.

The positive ion generation period ends when capacitor 78 charges sufficiently to reinitiate a high condition at the output of inverter 73i, the charging rate being determined by the setting of variable resistance 81. At that time, the output of inverter 73i returns to a low condition turning off transistor 62 and causing the output of the next inverter 73j to go high which in turn causes the output of inverter 73k to go low.

When the output of inverter 73k goes low, capacitor 79 is charged at a rate determined by the setting of variable resistance 84. After another off interval determined by the selected charging rate, capacitor 79 becomes sufficiently charged to reestablish a high condition at the input of inverter 73a and thereby reinitiate the cycle of operation which has been herein described. Such cycling continues in the manner described above until power on switch 37 is opened.

Referring now to FIG. 4, installation of the apparatus 11 in a clean room 102 or other location can be accomplished very simply and quickly. Control means housing 28 need not necessarily be close to the ionizing units 12 and may be located where it is readily accessible and visible to personnel, such as by attachment to a wall 103 among other suitable locations. The ionizing units 12 are positioned at spaced apart locations in the room 102 as determined from an analysis of the electrostatic charge build-up patterns of the particular room. Regions of charge build-up can be located and measured with instruments known to the art such as an electrostatic field meter.

In this example, the ionizing units 12 have a regular spacing of about 2.5 meters but different spacings including uneven spacings are appropriate in many cases where charge accumulation tends to be concentrated at specific locations. In many instances, it is most advantageous to locate the ionizing units 12 above the height of personnel by attaching the units to the ceiling 104. Many clean rooms 102 have a porous filter ceiling 104 through which a downward air flow 106 from a blower 107 is directed in order to continuously remove dust, vapors and other contaminants from the room. Such air flows typically exit through floor gratings 108. Location of the ionizing units 12 at the ceiling 104, with emitter units 19 and 21 directed downward, makes use of the air flow 106 to accelerate dispersal of ions away from the emitters and to carry the ions to work areas and materials or equipment at which suppression of electrostatic charge is most important. Referring again to FIG. 1, a very convenient mode of attaching the ionizing units 12 to ceiling 104 is by means of interlocking plastic strips 109 and 111 of the known form which adhere when pressed together, Scotchmate Type 400 manufactured by 3M Corporation, St. Paul, Minn. being an example. One such strip 109 may be secured against the top of each ionizing unit housing 13 with adhesive and the other strip 111 may be similarly secured to the underside of ceiling 104. A continuous band of the strip 111 may also be provided along the underside of ceiling 104 to facilitate repositionings of the ionizing units 12 in instances where that may be desirable. The ionizing units 12 may also be mounted at desired locations by means other than the interlocking strips 109 and 111.

Referring again to FIG. 4, the ionizing units 12 are preferably spaced outwardly from the walls 103 of the room 102. As previously discussed, air ionizers in general act to transfer electrical charge to particles of dust, smoke and the like which are then electrostatically attracted to nearby walls or other objects. This is basically very desirable as it is a form of air purification but spacing of the ionizing units 12 from walls 103 is usually advisable so that the resulting deposits on the walls are not concentrated at small areas adjacent the units.

While the invention has been described with respect to a specific embodiment or example, many variations are possible and it is not intended to limit the invention except as defined in the following claims.

We claim:

1. In a method of controlling the ion content of air within a predetermined region including the steps of periodically generating positive air ions at a first location and periodically generating negative air ions at a second spaced apart location during the intervals between periods of positive ion generation and wherein said positive and negative ions disperse outwardly from said first and second locations respectively and intermix within said region, the further step comprising:
   delaying said intermixing of said ions by delaying each period of ion generation for a predetermined time interval following termination of the preceding period of ion generation.

2. The method of claim 1 including the further step of controlling the distance from said first and second locations at which said positive and negative ions become intermixed by selection of the durations of said predetermined time intervals.

3. The method of claim 1 wherein each of said periods of ion generation is delayed, following termination of the preceding period of ion generation, for a predetermined time interval in the range from about 0.5 seconds to about 10 seconds.

4. The method of claim 1 including the further steps of adjusting the duration of said predetermined time interval during which said periods of positive ion generation are delayed, and separately and independently adjusting the duration of said predetermined time interval during which said periods of negative ion generation are delayed.

5. The method of claim 1 including the further steps of separately selecting the durations of said periods of positive and negative ion generations, separately selecting the durations of said predetermined time intervals during which periods of positive ion generation and periods of negative ion generation are delayed, and separately selecting the rate of ion generation during periods of positive ion generation and the rate of ion generation during periods of negative ion generation whereby preferred concentrations of each type of ion are established at a predetermined distance from said first and second locations.

6. A method of adjusting the concentrations of positive and negative ions in the air at a predetermined region comprising the steps of:
   generating positive ions at a first location during repetitive time periods of selected duration,
   generating negative ions at a second spaced apart location during repetitive time periods of selected duration that alternate with said periods of positive ion generation,
   delaying each period of ion generation at said first location for a selected time interval following the preceding period of ion generation at said second location, and
   delaying each period of ion generation at said second location for a selected time interval following the preceding period of ion generation at said first location.

7. In apparatus for controlling the concentrations of positive and negative ions within a volume of air, having at least one pair of spaced apart air ionizing electrodes including a positive electrode and a negative electrode, means for applying positive high voltage to said positive electrode, means for applying negative high voltage to said negative electrode, and control means for cyclically and alternately actuating said positive high voltage means and said negative high voltage means, the improvement comprising:
   means for delaying each actuation of said positive high voltage means for an interval following the preceding actuation of said negative high voltage means, and
   means for delaying each actuation of said negative high voltage means for an interval following the preceding actuation of said positive high voltage means.

8. The apparatus of claim 7 further including means for selectively varying the duration of said interval for which actuations of said positive high voltage means are delayed, and means for separately and selectively varying the duration of said interval for which actuations of said negative high voltage means are delayed.

9. The apparatus of claim 7 further including means for selectively varying the duration of said actuations of said positive high voltage means, and means for separately and selectively varying the duration of said actuations of said negative high voltage means.

10. The apparatus of claim 7 further including means for separately and independently varying the magnitudes of said positive high voltage and said negative high voltage.

11. The apparatus of claim 7 wherein said control means includes:
    means for selectively changing the duration of said actuations of said positive high voltage means,
    means for selectively changing the duration of said actuations of said negative high voltage means,
    means for selectively changing said interval for which actuation of said positive high voltage means is delayed following the preceding actuation of said negative high voltage means,
    means for selectively changing said interval for which actuation of said negative high voltage means is delayed following the preceding actuation of said positive high voltage means,
    means for selectively changing the magnitude of said positive high voltage, and
    means for selectively changing the magnitude of said negative high voltage.

12. The apparatus of claim 7 having a plurality of said pairs of spaced apart positive and negative air ionizing electrodes, said positive high voltage means having a plurality of separate positive high voltage generators each being connected to a separate one of said positive electrodes, said negative high voltage means having a plurality of negative high voltage generators each being connected to a separate one of said negative electrodes, said positive and negative high voltage generators being actuatable by relatively low voltage actuation signals, and wherein said control means alternately transmits said actuation signals to said positive high voltage generators and said negative high voltage generators.

13. The apparatus of claim 12 including a plurality of spaced apart bipolar ionizing units each including a separate one of said pairs of positive and negative ionizing electrodes together with one of said positive high voltage generators and one of said negative high voltage generators, each of said units having means for securing the unit at a different selected location within a room, and conductor means for transmitting said relatively low voltage actuation signals from said control means to each of said units.

14. The apparatus of claim 7 wherein said control means includes an electrical circuit having:

a plurality of signal inverters each having an input and an output and being of the type wherein the output is at a high signal condition when the input is at a low signal condition and wherein the output is at a low signal condition when the input is at a high signal condition, said inverters being connected to form a closed loop signal path wherein a change of condition at any of said inverters progressively initiates changes of condition at the others thereof around said closed loop, means for actuating said positive high voltage means in response to a predetermined signal condition at a first point in said closed loop signal path, means for actuating said negative high voltage means in response to a predetermined signal condition at a second point in said closed loop signal path, and wherein said means for delaying each actuation of said positive high voltage means delays progression of said changes of condition from said second point in said closed loop signal path to said first point therein, and wherein said means for delaying each actuation of said negative high voltage means delays progression of said changes of condition from said first point in said closed loop signal path to said second point therein.

15. Apparatus for controlling air ion content within a region comprising:

at least a pair of spaced apart air ionizing electrodes each having at least one sharp point exposed to said air, a positive high voltage generator connected to a first of said electrodes, a negative high voltage generator connected to the second of said electrodes, first control means for selecting a first ion generation delay period, second control means for selecting a second ion generation delay period, third control means for selecting a positive ion generation period, fourth control means for selecting a negative ion generation period, and timing circuit means for alternately actuating said positive high voltage generator and said negative high voltage generator to produce a repetitive ion generation cycle during which positive ions are generated for said positive ion generation period and then ion generation ceases for said first delay interval after which negative ions are generated for said negative ion generation period and then ion generation ceases for said second delay interval.

16. The apparatus of claim 15 further including:

fifth control means for adjusting the magnitude of the positive high voltage applied to said first electrode by said positive high voltage generator, and sixth control means for separately adjusting the magnitude of the negative high voltage applied to said second electrode by said negative high voltage generator.

* * * * *